(12) United States Patent
Ooteghem

(10) Patent No.: US 6,942,998 B1
(45) Date of Patent: Sep. 13, 2005

(54) PROCESS FOR GENERATION OF HYDROGEN GAS FROM VARIOUS FEEDSTOCKS USING THERMOPHILIC BACTERIA

(75) Inventor: Suellen Van Ooteghem, Morgantown, WV (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 440 days.

(21) Appl. No.: 10/141,863

(22) Filed: May 10, 2002

Related U.S. Application Data

(63) Continuation-in-part of application No. 09/618,462, filed on Jul. 18, 2000, now abandoned.

(51) Int. Cl.⁷ ................................................ C12P 3/00
(52) U.S. Cl. ...................................... 435/168; 435/170
(58) Field of Search ................................ 435/168, 170

(56) References Cited

PUBLICATIONS

Patel et al., Arch. Microbiol. (1985), vol. 141, pp. 63–69.*
Huber et al., Arch. Microbiol. (1986), vol. 144, pp. 324–333.*
Adams M.W.W., Chemtech, Nov. 1991, pp. 692–699.*
Gerhardt et al., "Manual of Method for general Bacteriology", p. 75, 1981. ASM.*
Balows et al., The Prokaryotes:, 1992, pp. 3809–3815.*

* cited by examiner

*Primary Examiner*—Irene Marx
(74) *Attorney, Agent, or Firm*—Joy Alwan; Thomas G. Anderson; Paul A. Gottlieb

(57) ABSTRACT

A method for producing hydrogen gas is provided comprising selecting a bacteria from the Order Thermotogales, subjecting the bacteria to a feedstock and to a suitable growth environment having an oxygen concentration below the oxygen concentration of water in equilibrium with air; and maintaining the environment at a predetermined pH and at a temperature of at least approximately 45° C. for a time sufficient to allow the bacteria to metabolize the feedstock.

18 Claims, 2 Drawing Sheets

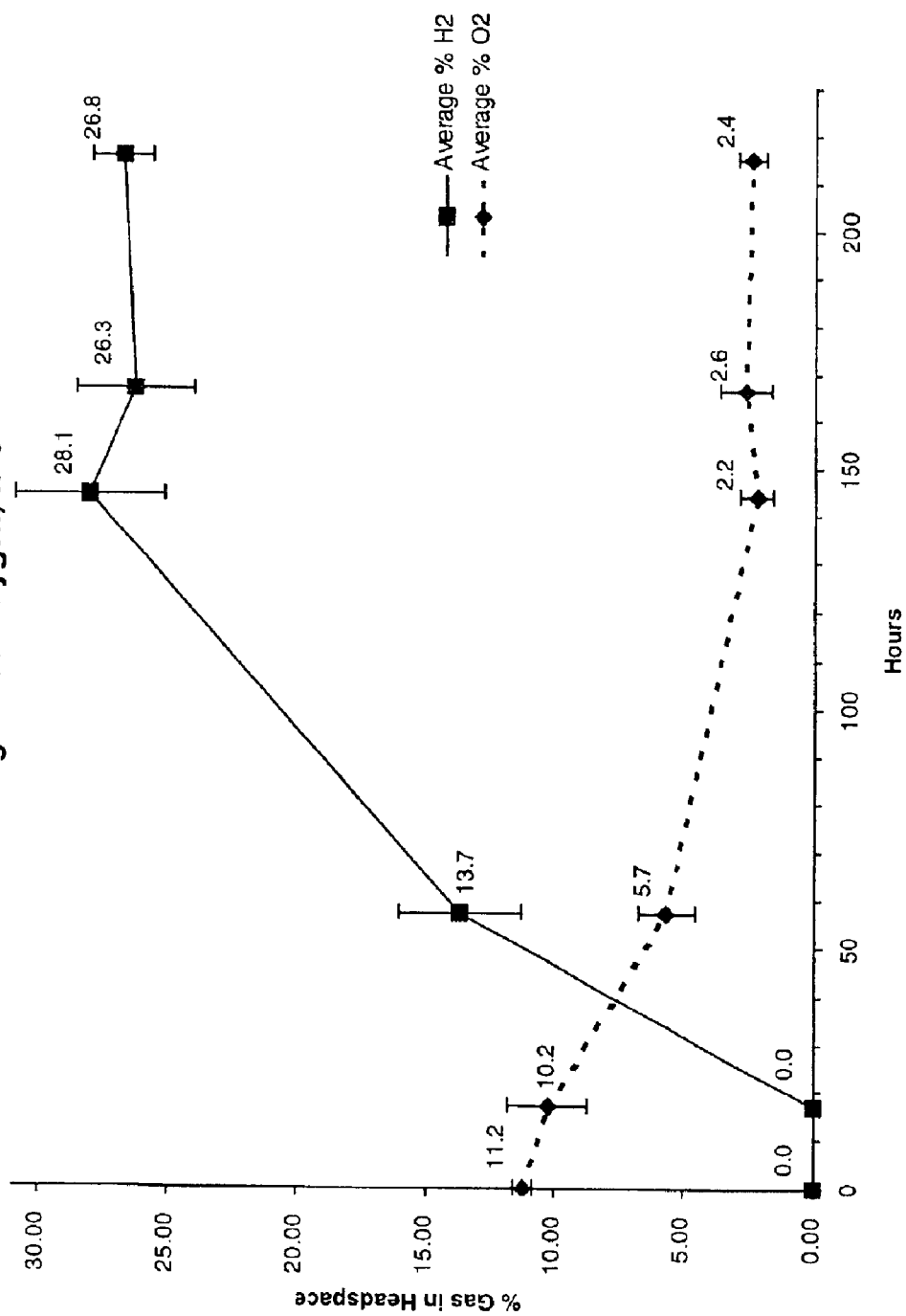

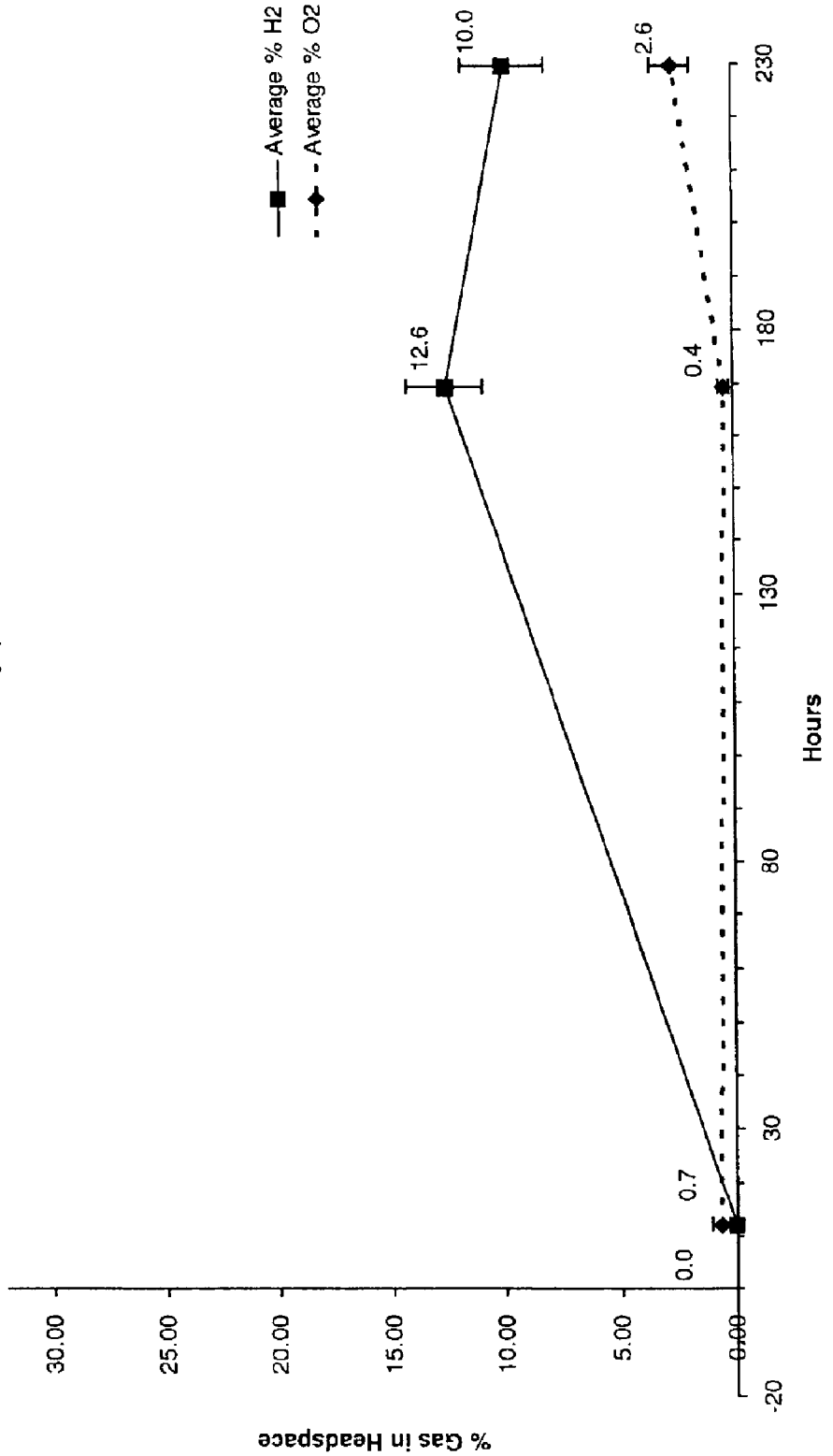

PROCESS FOR GENERATION OF HYDROGEN GAS FROM VARIOUS FEEDSTOCKS USING THERMOPHILIC BACTERIA

This application is a continuation-in-part of 09/618,462, filed Jul. 18, 2000, since abandoned.

CONTRACTUAL ORIGIN OF THE INVENTION

The United States Government has rights in this invention pursuant to an employment relationship between the inventor and the United States Department of Energy.

BACKGROUND OF THE INVENTION

1. Field of the Invention

This invention relates to a method for using bacteria to produce hydrogen gas, and more particularly this invention relates to a method for using thermophilic bacteria to generate hydrogen gas from a wide variety of feedstocks.

2. Background of the Invention

Hydrogen gas holds promise as the fuel of the future. The U.S. currently consumes 3.6 trillion cubic feet (TCF) of hydrogen gas annually, with a worldwide consumption of about three times that amount. The U.S. demand alone is expected to increase by 40% to 5.0 TCF in the next five years.

Most of the hydrogen gas produced throughout the world is made from synthesis gas generated either by reformation of natural gas or from the gasification of coal. Not only are these processes costly, but they are hostile to the environment. Furthermore, these methods use fossil fuels, which are non-renewable.

Biological processes have been used previously to generate hydrogen gas. Biological processes are particularly attractive because renewable feedstocks (i.e., biomass, even organic waste streams) are utilized. Research in this area has concentrated on three different approaches:

1) Using photosynthetic organisms to split water;

2) Using fermentative bacteria to digest hydrocarbons;

3) Using a combination of bacteria in which some of the bacteria digest the complex hydrocarbons to make an appropriate feedstock for the hydrogen-producing bacteria.

However, and as discussed more fully, infra, these efforts have not yet resulted in commercial success because of one or more problems. In some cases, the metabolic processes that produce hydrogen gas are end-product or by-product inhibited, while in other cases the growth rate of the bacteria is end-product or by-product inhibited. Still in other cases, the range of suitable feedstocks is narrow, or the production of undesirable gases is high. In some processes, the rate of hydrogen gas production is very low, while in all cases faster rates are highly desirable.

For example, photosynthetic processes exist (U.S. Pat. No. 5,804,424 to Kaplan et al; U.S. Pat. No. 4,921,800 to Vatsala, and U.S. Pat. No. 4,919,813 to Weaver) whereby photosynthetic organisms (such as algae or microalgae) use light to convert water into hydrogen gas and oxygen gas. However, the yields of hydrogen gas are very low in these instances because one of the end products of the reaction, oxygen gas ($O_2$), Irreversibly inhibits the hydrogenase enzyme responsible for hydrogen gas production. Even a very small amount of oxygen gas produced as a byproduct is sufficient to shut down the entire hydrogen gas production system by inactivating the hydrogenase enzyme. Thus, the amount of hydrogen gas produced is minimal, rarely exceeding 10 ppm. Efforts to prevent this oxygen gas inhibition by modification of the hydrogenase enzyme have met with only modest success. These altered hydrogenases can only tolerate 2% oxygen gas concentration.

Pond scum has been utilized recently to produce hydrogen gas at a rate of 3 ml/l-hour. A. Melis, et al., "Sustained Photobiological Hydrogen Gas Production Upon Reversible Inactivation of Oxygen Evolution in the Green Alga," *Proceedings of the 1999 U.S. DOE Hydrogen Program Review*, pp. 1–19. However, this was accomplished only while maintaining an oxygen-free environment for the algae and only for short time spans up to four days.

Another approach to producing hydrogen gas is the process of fermentation. Processes utilizing monocultures of various mesophilic bacteria produce hydrogen gas as a byproduct of anaerobic fermentative degradation of simple sugars (Roychowdhury, U.S. Pat. No. 4,480,035) or a combination of either formic acid or a formate plus a nitrogen source (Sanford, U.S. Pat. No. 5,834,264). Attentively, glucose or glucose-containing polysaccharide feedstocks are utilized (Taguchi, U.S. Pat. No. 5,350,692). These processes confer advantages over photosynthetic processes because fermentative processes use less water, require no direct input of solar energy, and eliminate the need for a container with a large translucent surface area. Fermentative mesophilic bacteria only need an input stream consisting of an appropriate aqueous medium and substrate and an output stream to remove the generated waste products and gases. Unfortunately, monocultures of mesophilic bacteria may be easily contaminated. This is a major drawback in an industrial-scale fermenter where complete sterilization is difficult and where contamination is almost unavoidable.

A variation of the fermentation approach has been to co-culture a number of different types of bacteria, where the net effect is to produce hydrogen gas as a by-product of fermentation of various carbohydrates or even sludge. (Ueno, U.S. Pat. No. 5,464,539). Co-culture with photosynthetic organisms has also been described. (Weaver, U.S. Pat. No. 4,919,813). Some of these processes produce noxious gases, such as hydrogen sulfide ($H_2S$) and methane ($CH_4$), along with other gases that would need to be separated from the hydrogen. Composting (i.e., partial decomposition) may be required as a time-consuming preliminary step to predigest the Initial feedstock and form more simple compounds that can then be utilized to produce hydrogen.

Attempts have been made to utilize mesophilic and thermophilic bacteria in hydrogen gas production processes. (See for example, M.W.W. Adams, CHEMTECH, November 1991, pp. 692–699.) Such bacteria as *Pyrococcus furiosus*, *Pyrodictium brockii* and *Thermotoga matitima* were examined. However, the hydrogenase system of the *P. brockii* and *T. maritima* showed a preference for $H_2$ oxidation, versus $H_2$ evolution. Also, the thermostability of *T. maritima* enzyme appeared inferior vis-a-vis *P. furiosus*.

A need exists in the art for a biological process for generating hydrogen gas on an industrial scale. The process should utilize a wide variety of hydrocarbon sources. Furthermore, the process should maximize hydrogen gas production and minimize hydrogen sulfide gas production. The process should have an inherent feature for minimizing its contamination.

SUMMARY OF THE INVENTION

An object of the present invention is to provide a process for producing hydrogen that overcomes many of the disadvantages of the prior art.

Another object of the present invention is to provide a robust catabolic process for producing hydrogen wherein a single species or several species from a single Order are cultured. A feature of the invention is that the organism is eurytolerant. An advantage of the invention is that stringent environmental controls such as air-tight environs, stringent levels of nutrients and media, and predigestion are not required. Another advantage of the process is that hydrogen is produced with minimal production of nitrous oxides ($NO_x$), sulfur oxides ($SO_x$), CO and $CH_4$, all of which are typically generated when hydrogen is produced via hydrocarbon gasification.

Yet another object of the present invention is to provide a process for producing hydrogen using thermophilic bacteria. A feature of the invention is that the process can utilize a variety of hydrocarbons as its feedstock. Other features of the invention are that the pH of the bioreaction is controlled, that the concentrations of potential sulfur-donors in the feedstock and aqueous medium are controlled, and that measured and limited amounts of oxygen gas are Introduced Into the process which the thermophilic organisms can either use or tolerate as facultative anaerobes and which oxygen gas may reduce the tendency to form hydrogen sulfide. An advantage of this invention is that hydrogen production is maximized while the production of hydrogen sulfide gas is minimized.

Still another object of the present invention is to provide a method of waste treatment that is also an environmentally-friendly process for producing hydrogen gas. A feature of the invention is that bacteria used in this process are omnivorous, and as such, the feedstock may consist of items from any one of a number of classes of complex hydrocarbons: such as starch, any one of a number of sugars, xylans, and/or celluloses, any one of a number of amino acids, long chain fatty acids, proteins, oils (including petroleum products) and combinations thereof. An advantage of this process is that the organisms incorporated in the process can utilize very complex hydrocarbons without requiring pre-processing to produce simple sugars or their catabolites. Therefore, the process is well suited to convert a wide variety of waste streams and biomass into hydrogen gas.

Another object of the present invention is to provide a controllable biological process for producing hydrogen gas from a wide variety of complex hydrocarbons; at higher rates per unit volume; with reduced sensitivity to the presence of $O_2$; with little sensitivity to the generated $H_2$; with minimal interference from other organisms; plus a low production of $CO_2$ and $H_2S$. A feature of this invention is that it operates using high temperatures, which reduce the risk of methane production and hydrogen sulfide production by other types of bacteria. An advantage of this process is that environmentally-unfriendly production of methane gas and hydrogen sulfide gas is minimized without resorting to composting the stock materials, without excessively limiting the range of feedstocks, and without resorting to other procedures to reduce or eliminate methanogenic bacteria and sulfur-reducing bacteria or their activities. Because few other organisms are capable of growth or even life at these temperatures, maintaining clean cultures, even in industrial-scale operations, is more feasible. Also, the desired thermophilic organisms remain viable for months at room temperature, but only grow when the temperature is elevated. Therefore, control and containment of the organism is simplified.

Still another object of the present invention is to provide a process which uses bacteria of the Order Thermotogales, to produce hydrogen gas in useful quantities. A feature of the invention is that the process utilizes physiological buffers and titration to maintain a pH in the reaction environment. An advantage of the process is that hydrogen can be continuously produced at rates above about 5 ml/l-hour.

Still another object of the present invention is to provide a biological process for producing hydrogen gas wherein the process utilizes facultative anaerobic bacteria which are also thermophilic. A feature of the invention is that the process can tolerate and may even use oxygen. An advantage of the process is its applicability to industrial situations. Another advantage is that the presence of oxygen may reduce the formation of $H_2S$ concomitantly generated.

Yet another object of the present invention is to provide a process for producing hydrogen gas that operates at subpyrolytic temperatures. A feature of the invention is that the process uses catabolism of hydrocarbons to produce hydrogen gas and carbon dioxide in a ratio of nearly 2:1. An advantage of the process is that unlike thermal processes, very little $NO_x$, $SO_x$, CO and $CH_4$ is produced.

Briefly, a process for producing $H_2$ is provided comprising confining bacteria from the Order Thermotogales to an environment suitable for allowing the bacteria to undergo metabolism; maintaining the environment at an oxygen concentration below the oxygen concentration of water in equilibrium with air; and removing hydrogen from the environment during the metabolism.

The invention also provides for a method for producing $H_2$ comprising selecting a bacteria from the Order Thermotogales; subjecting the bacteria to an environment containing a feedstock and a media, wherein the media contains oxygen gas in a concentration below the oxygen concentration of water in equilibrium with air; and maintaining the environment at a temperature, pressure and pH sufficient to allow the bacteria to metabolize the feedstock.

Additional objects, features and advantages are found throughout the specification or will become apparent to those skilled in the art upon examination of the description that follows. Other objects may be learned by the practice of this invention.

BRIEF DESCRIPTION OF THE DRAWINGS

The present invention together with the above and other objects and advantages may best be understood from the following detailed description of the embodiment of the invention illustrated in the drawings, wherein:

FIG. 1 shows the relationship of headspace hydrogen and oxygen concentrations verses time when the initial oxygen concentration is high.

FIG. 2 shows the percent of headspace hydrogen and oxygen concentrations verses time when the headspace oxygen concentration is low.

DETAILED DESCRIPTION OF THE INVENTION

Instead of using algae, mesophilic bacteria or co-cultures of bacteria, thermophilic bacteria of the Order Thermotogales are utilized for the production of hydrogen gas ($H_2$). The inventor has determined experimentally that bacteria of the Order Thermotogales, previously thought to be viable only in an anaerobic fermentative environment, can be used to produce hydrogen gas in a process that can tolerate relatively high concentrations of oxygen without apparent loss of hydrogen-producing ability. Some of these types of organisms can even tolerate oxygen levels very close to that of ambient air for short periods of time at room temperature.

In light of the forgoing, surprisingly and unexpectedly, the inventor has found that the invented process is not a true fermentative process, despite wide-spread claims in the scientific literature that incorrectly label the Order Thermotogales as obligate (true) anaerobes. Thus, in industrial-scale systems, small leaks in the fermentation apparatus will not upset or kill the culture.

The inventor speculates that any residual oxygen gas that is present combines with carbon atoms as the hydrocarbon feedstock is metabolized, thereby minimizing the tendency to form sulfides from the sulfates in solution. Moreover, the presence of oxygen gas in this process may reduce the formation of $H_2S$ by any processes that could create it. The invented process illustrates that each of the members of the Order Thermotogales can be utilized with specific feedstocks to optimize yield, so that while one particular Species may produce more hydrogen when the feedstock is a simple sugar, others may prefer more complex hydrocarbons, carbohydrates, proteins or oils. Co-cultures of complimentary Species may act in concert to completely degrade hard-to-utilize waste materials to produce hydrogen gas. Furthermore, and as noted elsewhere in this specification, the invented protocol generates hydrogen gas ($H_2$) at a 2:1 ratio with $CO_2$, versus the expected 1:1 ratio.

Thermophilic (heat-loving) bacteria become active in a temperature range that is much higher than for most other organisms. There is no one temperature range that is applicable to all thermophilic organisms. This is particularly true for members of the Order Thermotogales. Below a certain temperature, these organisms change form and appear coccoid (spherical). At higher temperatures these rod-shaped organisms metabolize, and at some temperature begin reproduction. After reaching a peak in organism growth at an optimal temperature, organism growth decreases with further increases in temperature. The range of temperatures over which an organism is seen to grow is referred to for the purposes of this document as the "permissive range" for that particular Species. The permissive range and the optimum temperature differs for each species within the Order Thermotogales.

Bacteria of the Order Thermotogales can be easily maintained as a monoculture and readily Inactivated and reactivated after short-term storage at room temperature. When the reaction temperature is elevated to the permissive range, the organisms readily grow and produce hydrogen gas. At this elevated temperature, most other bacteria are not capable of surviving. Thus, the maintenance of clean monocultures (i.e., cultures not contaminated with other bacteria) is facilitated. Conversely, to deactivate the bacteria, the reaction temperature is lowered to below the permissive range. The organisms cease growth, and hydrogen production stops. The organisms can be stored in a sealed bottle for several months with no harm or apparent loss of viability to the organisms. To kill these organisms they are sparged with air at 20° C. for several hours while the temperature is elevated to the permissive range.

At temperatures in the permissive range, the bacteria convert a wide array of feedstocks into free hydrogen gas ($H_2$) and lesser quantities of carbon dioxide ($CO_2$). Only trace quantities of hydrogen sulfide ($H_2S$) are generated if the concentrations of elemental sulfur and sulfide salts available to the bacteria in the medium and feedstock are sufficiently low.

Like the permissive range for temperature, there are "permissive ranges" for both pH and oxygen. The organisms function best at an optimal pH and oxygen level, with diminishing functionality as the measured pH and oxygen levels differ from the optimal. The permissive range for both pH and oxygen levels also differs for each Species within the Order Thermotogales.

The pH at which the bacterial incubation process is conducted is extremely important, and greatly affects hydrogen gas yields. Titration or the addition of a physiological buffer to the incubation solution helps to maintain the pH and improves hydrogen yields. The optimal incubation pH (relative to optimal hydrogen production) is determined experimentally for each Genus and Species of bacteria in the Order Thermotogales. While the optimum pH will vary from Species to Species within the Order, a pH of between 4 and 10 is a good starting point to determine pH sensitivity. Preferably, pH specificity is determined empirically for each Species incorporated into the protocol. It should be noted that per convention, pH is measured at 20° C., versus the actual running temperature.

Process Detail

A culture of bacteria of the Order Thermotogales is placed in a vessel along with a feedstock plus an aqueous medium. Under the incubation conditions tested, with over 3500 experiments conducted by the inventor, it was found that the bacteria produce virtually no nitrogen oxides, sulfur oxides, carbon monoxide, or methane gas. Reduced production of $H_2S$ is also obtained when elemental sulfur and sulfide salts are not available in the incubation medium.

Specifically, a culture of these bacteria is placed in a vessel along with an aqueous medium plus a feedstock. The aqueous medium contains a mixture of water, salts, vitamins, physiological buffers and biological cofactors. The feedstock is a material or waste that consists of or contains any combination of sugars (monosaccharides or polysaccharides) or complex hydrocarbons. At temperatures above 45° C. and at lowered dissolved oxygen levels (reduced oxygen gas in the headspace gases relative to ambient air), the bacteria can convert a wide array of feedstocks into free hydrogen gas ($H_2$) and lesser quantities of carbon dioxide ($CO_2$). Only trace quantities of hydrogen sulfide ($H_2S$) are generated if the sulfur (elemental or sulfide salts) content of the feedstock is sufficiently low. Hydrogen gas production does not appear to be end-product ($H_2$) inhibited. To maintain continuous production, pH must be controlled by titration or with a physiological buffer. (A physiological buffer is one that acts to maintain a constant pH and is not toxic to living tissue.) This process does not require completely anaerobic conditions within the reactor, as in true fermentative processes.

Prior to incubation and concomitant hydrogen production, nitrogen, or an inert gas (which is not likely to be used by the organisms), is sparged into the aqueous medium to reduce the dissolved oxygen concentration in the aqueous medium to a level below that of water in equilibrium with ambient air. While the amount of oxygen in the aqueous medium is less than that normally found in water that is in equilibrium with ambient air, some oxygen remains. During the sparging process, oxygen is also displaced from the headspace, thereby reducing the opportunity for reintroduction of oxygen into the aqueous medium. By capping or sealing the container immediately, oxygen is prevented from re-entering the bottle.

As an option, an indicator dye that changes color in the presence of elevated concentrations of oxygen gas may be added to the aqueous medium. Examples of such indicator dyes include Resazurin or Methyl Green. However, once the appropriate amount of time has been empirically determined, the indicator dyes can be replaced by simply sparging for the amount of time empirically determined as adequate to reduce the oxygen content sufficiently.

The role of oxygen gas ($O_2$) in the process of hydrogen gas generation has not yet been determined. However, it is reasonable to consider dissolved oxygen concentrations in terms of a "permissive range", which may differ with each Species. Generally, however, the dissolved oxygen concentrations in the aqueous medium are between about 0.2 mg/liter and 2.8 mg/liter. Oxygen levels of between 0.1 and 15 volumetric percent of the gas in the head space of the reaction vessel is suitable.

In a batch culture, the maximum hydrogen gas concentration generated by most hydrocarbon sources occurs between 3–7 days from the start of incubation. The chief gases produced are hydrogen (as much as 25–35% volumetric percent of the head space gas), and carbon dioxide (approximately ½ the amount of hydrogen produced), and small quantities (ppm) of hydrogen sulfide.

In a continuously growing culture, it is theoretically possible that hydrogen product might reach as high as 60% with most of the balance being carbon dioxide. Initially nitrogen is needed to displace the oxygen from both the aqueous medium and the headspace; however, once sufficient hydrogen and carbon dioxide have evolved, the nitrogen sparge is no longer needed. Hydrogen and carbon dioxide gases would comprise almost the entire gas stream produced in a continuous production scheme.

In a continuously operating bio-reactor, the constituents of the aqueous medium and the headspace can be continuously or intermittently replenished, withdrawn or adjusted, as can the pH, percent dissolved oxygen, and temperature.

As noted supra, process temperatures of above 45° C. are suitable. With the Species tested to date, the inventors have determined a preferable temperature range of approximately 55° C. and 90° C.

Thermotogales
Order Detail

Either the literature or test results indicate that hydrogen production occurs with all nineteen readily available (and thus, testable) members (shown below) of the Order Thermotogales. This suggests that hydrogen production is a defining characteristic of members of this entire Order. All members of the Order Thermotogales are considered suitable for use in the invented hydrogen producing process.

Several resources provide general protocols for establishing and maintaining viable cultures of bacteria of the Order Thermotogales for innoculation, including R. Huber et al. "The order Thermotogales" in *The Prokaryotes*. Eds. A Balows, et al (Springer, Berlin, Heidelberg, N.Y., 1992); incorporated herein by reference. The following members of the Order Thermotogales are suitable for use in the invented hydrogen producing process:

*Thermotoga sp.* (DSMZ 4138)

*Thermotoga elfeii* (ATCC 51869, DSMZ 9442)

*Thermotoga hypogea* (DSMZ 11164)

*Thermotoga maritima* (DSMZ 3109)

*Thermotoga neapolitana* (from Naples) (ATCC 49049, DSMZ 4359)

*Thermotoga neapolitana* (from Africa) (DSMZ 5068)

*Thermotoga subterranea* (DSMZ 9912)

*Thermotoga thermarum* (DSMZ 5069)

*Petrotoga miotherma* (ATCC 51224, DSMZ 10691)

*Petrotoga mobilis* (DSMZ 10674)

*Thermosipho sp.* (DSMZ 6568)

*Thermosipho africanus* (DSMZ 5309)

*Thermosipho melanesiensis* (DSMZ 6976)

*Fervidobacterium islandicum* (DSMZ 5733)

*Fervidobacterium nodosum* (DSMZ 5306)

*Fervidobacterium pennavorans* (DSMZ 9078)

*Fervidobacterium gondwanense* (DSMZ 13020)

*Geotoga petraea*

*Geotoga subterranea*

DSMZ=Deutsche Sammulung von Mikroorganismne und Zelikulturen GmbH (German Collection of Microorganisms and Cell Culture)

Nutrient and
Media Detail

An aqueous medium comprising water, salts, vitamins, physiological buffers, and biological cofactors are utilized. The aqueous medium is supplemented with a hydrocarbon source as the "feedstock".

Bacteria of the Order Thermotogales can utilize very complex hydrocarbons without requiring preprocessing to produce simple sugars or their catabolites. Therefore, feedstocks suitable for the invented process include materials, such as biomass or organic wastes, that consist of or contain any combination of: (1) sugars (monosaccharides and polysaccharides); (2) complex hydrocarbons, such as crude oil; (3) carbohydrates, such as starch; (4) xylans and celluloses; (5) amino acids; (6) proteins; and (7) long chain fatty acids.

Specific media formulations that have been demonstrated as suitable for specific members of the Order Thermotogales can be utilized in this process if the formulation is modified so that no elemental sulfur or sulfide salt is present. The elemental sulfur or sulfide salt is replaced with a compound such as cysteine, to provide any sulfur that might be needed by the bacteria. This modification will help minimize the production of hydrogen sulfide.

Any media chosen is likely to be modified by enriching the hydrocarbon source, and/or omitting any indicator dyes (such as Resazurin or Methyl Green).

All of the common fermentative catabolites (such as acetate salts) are also omitted from the media formulations.

The following are exemplary media which can be employed in the process.

| | |
|---|---|
| ATCC Medium 1658: | MMS Medium for *Thermotoga neap.* |
| ATCC Medium 1977: | *Thermotoga elfeii* Medium $NH_4Cl$ |
| ATCC Medium 1881: | *Petrotoge* Medium Trypticase |
| DSMZ Medium 88: | *Sulfolobus* Medium |
| DSMZ Medium 141: | *Methenogenium* Medium |
| DSMZ Medium 144: | *Thermoanaerobium* Medium |
| DSMZ Medium 343: | *Thermotoga* Medium |
| DSMZ Medium 483: | *Thermosipho africanus* Medium |
| DSMZ Medium 498: | *Thermotoga* II Medium |
| DSMZ Medium 501: | *Fervidobacterium islandicum* Medium |
| DSMZ Medium 613: | TF Medium |
| DSMZ Medium 644: | *Thermotoga elfeii* Medium |
| DSMZ Medium 688: | *Thermotoga subterranea* Medium |
| DSMZ Medium 718: | *Petrotoga* Medium |
| DSMZ Medium 740: | TF(A) Medium |
| DSMZ Medium 794: | *Thermatoga hypogea* Medium |

The following materials (see Demonstration Experiment) are likely to be found in a suitable medium for this process. Some of the constituents are consumed by the organisms and others are needed for the organism to prevent hyper- or hypo-tonicity and to maintain homeostasis. While exact concentrations of each constituent are not as important as its mere presence, the pH of the medium seems to require control to maintain high production rates.

Demonstration Experiment

The current known best practice protocol for preparation of the aqueous medium and for conducting a demonstration experiment is outlined below.

1. An exemplary aqueous medium is prepared using the following constituents and protocol. It should be noted that different concentrations of salts should be used for some bacteria of the Order Thermotogales that typically are found in an environment that contains either more or less salt than in the illustrated examples contained herein.

| Aqueous Medium (Use a different concentration of salts for some species; see examples) | |
|---|---|
| $H_2O$ | 1.0 L |
| $NH_4Cl$ | 1.0 gm |
| $K_2HPO_4$ | 0.3 gm |
| $KH_2PO_4$ | 0.3 gm |
| $MgCl_2 \times 6\ H_2O$ | 0.2 gm |
| $CaCl_2 \times 2\ H_2O$ | 0.1 gm |
| NaCl | 10.0 gm |
| KCl | 0.1 gm |
| Cysteine HCl | 1.0 gm |
| Trizma Base (optional) | 1.21 gm |
| Sodium Acetate (optional) | 0.5 gm |
| Yeast Extract | 2.0 gm |
| Trypticase (BBL 11921) | 2.0 gm |
| Resazurin (optional) | 0.5 mg |
| Vitamin Solution (described below) | 10.0 ml |
| Trace Element Solution (described below) | 10.0 ml |
| Vitamin Solution (This solution can be omitted for some species; see examples) | |
| $H_2O$ | 10 L |
| Biotin | 2.0 mg |
| Folic Acid | 2.0 mg |
| Pyridoxine HCl | 10.0 mg |
| Thiamine HCl | 5.0 mg |
| Riboflavin | 5.0 mg |
| Nicotinic Acid | 5.0 mg |
| Calcium D-(+)-Pantothenate | 5.0 mg |
| Cyanocobalamine | 0.1 µg |
| p-Aminobenzoic Acid | 5.0 mg |
| Thioctic Acid | 5.0 mg |
| Trace Element Solution (This solution can be omitted for some species: see examples) | |
| Nitrolotriacetic acid | 1.500 g |
| $MgSO_4 \times 7\ H_2O$ | 3.000 g |
| $MnSO_4 \times 2\ H_2O$ | 0.500 g |
| NaCl | 1.000 g |
| $FeSO_4 \times 7\ H_2O$ | 0.100 g |
| $CoSO_4 \times 7\ H_2O$ | 0.180 g |
| $CaCl_2 \times 2\ H_2O$ | 0.100 g |
| $ZnSO_4 \times 7\ H_2O$ | 0.180 g |
| $CuSO_4 \times 5H_2O$ | 0.010 g |
| $KAl(SO_4)_2 \times 12\ H_2O$ | 0.020 g |
| $H_3BO_3$ | 0.010 g |
| $Na_2MoO_4 \times 2H_2O$ | 0.010 g |
| $NiCl_2 \times 6\ H_2O$ | 0.025 g |
| $Na_2SeO_3 \times 5\ H_2O$ | 0.300 mg |
| Distilled water | 1000.000 ml |

2. The initial pH of the aqueous medium is adjusted with acid or base (e.g. HCl or NaOH) as appropriate for the selected species of bacteria.
3. In experimental situations, the aqueous medium is placed in a container that has an appropriate headspace and that can be sealed. An appropriate headspace is one that is large enough to collect the hydrogen gas. An example of a suitable container for bench-top analysis is a serum bottle with 150 ml capacity. In such situations, approximately 50 ml of medium is put in the bottle.
4. Approximately 0.25 grams of a feedstock are added to the reaction container. The feedstock contains one or more of the following: starch, cellulose, bagasse, carboxymethyl cellulose, hemicellulose, glucose, cellobiose, crude oil, amino acids, proteins or other hydrocarbon source.
5. Optionally, a physiological buffer (such as Trizma Base) is added to the solution to help maintain a constant pH. Maintaining the pH of the cultured medium either with a physiological buffer or by titration facilitates optimal hydrogen gas production.
6. An indicator dye (e.g., Resazurin or Methyl Green) may be added as an optional indicator to show when a high concentration of dissolved oxygen is present. When sufficient $O_2$ is removed by the purging procedure discussed in step 7, the solution turns colorless.
7. Excess oxygen is removed from the reaction chamber by sparging with an inert gas for a time sufficient to reduce the oxygen content in both the liquid and gaseous phases in the container. Application of heat will facilitate the sparging process. While sparging, the reaction container is heated, (e.g., by being placed in a hot oil bath) at approximately 100° C. for 5–10 minutes while the sparge gas is gently bubbled through the medium. If an indicator dye has been added, the sparging is stopped when the liquid medium goes colorless. Inasmuch as a standard serum bottle is utilized as the reaction vessel, sealing after sparging is nearly immediate. This helps prevent re-entry of oxygen into the reaction space.
8. The reaction chamber with its contents is then subjected to heat for a time sufficient to sterilize the contents. In this example, the chamber is sterilized at 134–138° C. for ½ hour.
9. The solution is then inoculated with bacteria of the Order Thermotogales, an example of which is *Thermotoga neapolitana* (Naples).
10. The bacteria are incubated for a time sufficient to produce hydrogen gas. Generally, suitable parameters include incubation times of between 3–9 days at a temperature of above 45° C., preferably above 55° C., and most preferably between 55° C. and 90° C. (with or without mixing) without elevating the pressure artificially.
11. Following incubation, gases in the headspace of the serum bottle, are withdrawn and analyzed using a hydrogen sensing device such as a gas chromatograph.
12. In a continuous fermentation, the hydrogen gas can be removed from the headspace and collected for analysis using a myriad of gas collection means, including gas-tight bags or containers.

This best practice demonstration experiment describes a basic process that can lead to the development of an industrial-scale production of hydrogen gas and carbon dioxide (2:1 v/v). The demonstration experiment starts with a liquor of 50 ml of the aqueous medium (as described above) and can produce at least 20 to 35 ml total hydrogen gas evolved in addition to the $CO_2$ and $H_2S$ in 3–7 days within a headspace of 110 ml. This is accomplished using a biological process that degrades complex hydrocarbons. No other process has been found that describes the use of members of the Order Thermotogales in combination with the described mixture of salts, vitamins, physiological buffers and biological cofactors for such rapid production of hydrogen gas.

The following examples are illustrative only. As such, the specific concentrations and ranges discussed therein should not be construed as limiting the scope of the claims, appended hereto.

EXAMPLE 1

The thermophilic bacteria, *Thermotoga neapolitana* (ATCC 49049, DSMZ4359 from Naples) was placed in a sealed container along with the medium described above, at the strength indicated above, pH 8.5, and with soluble starch as the feedstock. The container had 50 ml of liquor with a headspace of 110 ml, consisting initially of nitrogen gas with 5–12% oxygen gas. The hydrogen gas production in the headspace may be described as follows: (1) a cumulative $H_2$ production of 24.4 ml (in 110 ml of available headspace) in 85 hours of incubation; (2) a cumulative $H_2$ production rate of 2.61 ml/l-hour; and a calculated $H_2$ concentration of 221 ml/l. This production assumes that the feedstock was not rate-limiting and that the tests started when the sterile medium was inoculated.

EXAMPLE 2

A thermophilic bacteria, *Thermotoga neapolitana* (ATCC 49049, DSMZ 4359 from Naples), was placed in a sealed container along with a physiologically buffered solution of the medium described above, at the concentration noted, with a pH of 8.0, and with soluble starch as the feedstock. There was 50 ml of liquor with a headspace of 110 ml consisting initially of nitrogen gas with 5–12% oxygen gas. The hydrogen gas production can be described as follows: (1) a cumulative $H_2$ production of at least 33.7 ml (in 110 ml of available headspace) in 74 hours; (2) a cumulative $H_2$ production rate of at least 4.14 ml/l-hour; and (3) a calculated $H_2$ concentration of 306 ml/l. This production assumes that the feedstock was not rate-limiting and that the tests started when the sterile medium was inoculated.

EXAMPLE 3

A thermophilic bacteria, *Petrotoga mobilis* (DSMZ 10674), was placed in a sealed container along with the medium described above at double strength with a pH of 6.0 and cellobiose as the feedstock. There was 50 ml of liquor with a headspace of 110 ml consisting initially of nitrogen gas with 5–15% oxygen gas. The hydrogen gas production can be described as follows: (1) a cumulative $H_2$ production of 15.5 ml (in 110 ml of available headspace) in 248 hours; (2) a cumulative $H_2$ production rate of 0.567 ml/l-hour; and (3) a calculated $H_2$ concentration of 140 ml/l. This production assumes that the feedstock was not rate-limiting and that the tests started when the sterile medium was inoculated.

EXAMPLE 4

A thermophilic bacteria, *Thermotoga elfeii* (ATCC 51869, DSMZ 9442), was placed in a sealed container along with a buffered solution of the medium described above at the concentration noted, with a pH of 8.0, and with soluble starch as the feedstock. There was 50 ml of liquor with a headspace of 110 ml consisting initially of nitrogen gas with 3–12% oxygen gas. The hydrogen gas production can be described as follows: (1) a cumulative $H_2$ production of 31.6 ml (in 110 ml of available headspace) in 124 hours; (2) a cumulative $H_2$ production rate of at least 2.32 ml/l-hour; and (3) a calculated $H_2$ concentration of 287 ml/l. This production assumes that the feedstock was not rate-limiting and that the tests started when the sterile medium was inoculated.

EXAMPLE 5

A thermophilic bacteria, *Petrotoga miotherma* (ATCC 51224, DSMZ 10691), was placed in a sealed container along with the unbuffered medium described above at a pH of 8.0 and with potato starch as the feedstock. There was 50 ml of liquor with a headspace of 110 ml consisting initially of nitrogen gas with 0.4–13% oxygen gas. The hydrogen gas production can be described as follows: (1) a cumulative $H_2$ production of 12.9 ml (in 110 ml of available headspace) in 176 hours; (2) a cumulative $H_2$ production rate of 0.668 ml/l-hour; and (3) a calculated $H_2$ concentration of 118 ml/l. This production assumes that the feedstock was not rate-limiting and that the tests started when the sterile medium was inoculated.

EXAMPLE 6

A thermophilic bacteria, *Thermotoga sp.*(DSMZ 4138), was placed in a sealed container along with the medium described above at a pH of 8.0, and with dextrose as the feedstock. There was 50 ml of liquor with a headspace of 110 ml consisting initially of nitrogen gas with 3–15% oxygen gas. The hydrogen gas production can be described as follows: (1) a cumulative $H_2$ production of at least 0.56 ml (in 110 ml of available headspace) in 55 hours; (2) a cumulative $H_2$ production rate of at least 0.093 ml/l-hour; and (3) a calculated $H_2$ concentration of 50.9 ml/l. This production assumes that the feedstock was not rate-limiting and that the tests started when the sterile medium was inoculated.

EXAMPLE 7

A combination of thermophilic bacteria, *Thermotoga elfeii* (ATCC 51869, DSMZ 9442), *Thermotoga neapolitana* (ATCC 49049, DSMZ 4359) and *Thermotoga sp.* (DSMZ 4138), were placed in a sealed container along with a double strength medium compared to that described above, at a pH of 6.5 and with cellulose as the feedstock. There was 50 ml of liquor with a headspace of 110 ml consisting initially of nitrogen gas with 4–9% oxygen gas. The hydrogen gas production can be described as follows: (1) a cumulative $H_2$ production of 18.0 ml (in 110 ml of available headspace) in 146 hours; (2) a cumulative $H_2$ production rate of at least 1.12 ml/l-hour and (3) a calculated $H_2$ concentration of 163 ml/l. This production assumes that the feedstock was not rate-limiting and that the tests started when the sterile medium was inoculated.

EXAMPLE 8

The thermophilic bacteria, *Thermotoga hypogea* (DSMZ 11164) was placed in a sealed container along with a single strength medium compared as described above, at a pH of 9.0 and with dextrose as the feedstock. There was 50 ml of liquor with a headspace of 110 ml consisting initially of nitrogen gas with 0.5–8% oxygen gas. The hydrogen gas production can be described as follows: (1) a cumulative H2 production of 20.08 ml (in 110 ml of available headspace) in 179 hours; (2) a cumulative H2 production rate of at least 1.02ml/l-hour; and (3) a calculated H2 concentration of 182.5 ml/l. This production assumes that the feedstock was not rate-limiting and that the tests started when the sterile medium was inoculated.

EXAMPLE 9

The thermophilic bacteria, *Thermosipho africanus* (DSMZ 5309) was placed in a sealed container along with a double strength medium compared with the media described above, at a pH of 8.0 and with dextrose as the feedstock. There was 50 ml of liquor with a headspace of 110 ml consisting initially of nitrogen gas with 0.2–8% oxygen gas. The hydrogen gas production can be described as follows: (1) a cumulative H2 production of 21.99 ml (in 110 ml of available headspace) in 111 hours; (2) a cumulative H2 production rate of at least 1.80 ml/l-hour; and (3) a calculated H2 concentration of 199.9 ml/l. This production assumes that the feedstock was not rate-limiting and that the tests started when the sterile medium was inoculated.

EXAMPLE 10

The thermophilic bacteria, *Fervidobacterium pennavorans* (DSMZ 9078) was placed in a sealed container along with a one-tenth strength medium compared with the medium described above, at a pH of 8.0 and with cellobiose as the feedstock. There was 50 ml of liquor with a headspace of 110 ml consisting of 0.1–8% oxygen gas. The hydrogen gas production can be described as follows: (1) a cumulative H2 production of 17.68 ml (in 110 ml of available headspace) in 80 hours; (2) a cumulative H2 production rate of at least 2.01 ml/l-hour; and (3) a calculated H2 concentration of 160.7 ml/l. This production assumes that the feedstock was not rate-limiting and that the tests started when the sterile medium was inoculated.

EXAMPLE 11

The thermophilic bacteria, *Thermotoga subterranea* (DSMZ 9912) was placed in a sealed container along with DSMZ medium 344, a medium similar to that described in detail above, at a pH of 7.0 and with dextrose as the feedstock. There was 50 ml of liquor with a headspace of 110 ml consisting initially of nitrogen gas with 0.5–2% oxygen gas. The hydrogen gas production can be described as follows: (1) a cumulative H2 production of 19.49 ml (in 110 ml of available headspace) in 128 hours; (2) a cumulative H2 production rate of at least 1.38 ml/l-hour; and (3) a calculated H2 concentration of 177.2 ml/l. This production assumes that the feedstock was not rate-limiting and that the tests started when the sterile medium was inoculated.

EXAMPLE 12

The thermophilic bacteria, *Thermotoga maritima* (DSMZ 3109) was placed in a sealed container along with a single strength DSMZ medium 688, a medium similar to that described above, at a pH of 7.0 and with dextrose as the feedstock. There was 50 ml of liquor with a headspace of 110 ml consisting initially of nitrogen gas with 1–5% oxygen gas. The hydrogen gas production can be described as follows: (1) a cumulative H2 production of 6.31 ml (in 110 ml of available headspace) in 128 hours; (2) a cumulative H2 production rate of at least 0.448 ml/l-hour; and (3) a calculated H2 concentration of 57.4 ml/l. This production assumes that the feedstock was not rate-limiting and that the tests started when the sterile medium was inoculated.

EXAMPLE 13

The thermophilic bacteria, *Thermosipho melanesiensis* (DSMZ 12029) was placed in a sealed container along with single strength DSMZ medium 344, a medium similar to that described in detail above, at a pH of 7.0 and with dextrose as the feedstock. There was 50 ml of liquor with a headspace of 110 ml consisting initially of nitrogen gas with 1–4% oxygen gas. The hydrogen gas production can be described as follows: (1) a cumulative H2 production of 17.97 ml (in 110 ml of available headspace) in 128 hours; (2) a cumulative H2 production of at least 1.28 ml/l-hour; and (3) a calculated H2 concentration of 163.4 ml/l. This production assumes that the feedstock was not rate-limiting and that the tests started when the sterile medium was inoculated.

EXAMPLE 14

The thermophilic bacteria, *Thermotoga neapolitana* (africa) (DSMZ 5068) was placed in a sealed container along with a single strength DSMZ medium 344, a medium similar to the medium described above, at a pH of 7.0 and with dextrose as feedstock. There was 50 ml of liquor with a headspace of 110 ml consisting initially of nitrogen gas with 1–4% oxygen gas. The hydrogen gas production can be described as follows: (1) a cumulative H2 production of 13.63 ml (in 110 ml of available headspace) in 175 hours; (2) a cumulative H2 production rate of at least 0.708 ml/l-hour; and (3) a calculated H2 concentration of 123.9 ml/l. This production assumes that the feedstock was not rate-limiting and that the tests started when the sterile medium was inoculated.

EXAMPLE 15

The thermophilic bacteria, *Fervidobacterium gondwanense* (DSMZ 13020) was placed in a sealed container along with a single strength DSMZ medium 740, a medium similar to the medium described above, at a pH of 7.0 and with dextrose as the feedstock. There was 50 ml of liquor with a headspace of 110 ml consisting initially of nitrogen gas with 0.7–4% oxygen gas. The hydrogen gas production can be described as follows: (1) a cumulative H2 production of 6.57ml (in 110 ml of available headspace) in 14 hours; (2) a cumulative H2 production rate of at least 5.4 ml/l-hour; and (3) a calculated H2 concentration of 59.72 ml/l . This production assumes that the feedstock was not rate-limiting and that the tests started when the sterile medium was inoculated.

EXAMPLE 16

The thermophilic bacteria, *Thermotoga neapolitana* (DSMZ 4359 from Naples) was placed in a sealed container along with ATCC medium 1977 and no additional feedstock was added beyond the proteins, amino acids and hydrocarbons characteristic of this medium. The bacteria had previously been habituated to a medium containing only minimal amounts of carbohydrates. There was 50 ml of liquor with a headspace of 110 ml in the container consisting initially of nitrogen gas with 5–12% oxygen gas. The hydrogen gas production can be described as follows: (1) a cumulative H2 production of 5.12 ml (in 110 ml of available headspace) in 137 hours; (2) a cumulative H2 production rate of at least 0.339 ml/l-hour; and (3) a calculated H2 concentration of 46.54 ml/l. This production assumes that the feedstock was not rate-limiting and that the tests started when the sterile medium was inoculated.

EXAMPLE 17

The thermophilic bacteria, *Thermotoga elfeii* (ATCC 51869, DSMZ 9442) was placed in a sealed container along with ATCC medium 1977 at a pH of 8.0 and with West Virginia Crude Oil as the feedstock. There was 50 ml of liquor with a headspace of 110 ml consisting initially of nitrogen gas with 4–17% oxygen gas. The hydrogen gas production can be described as follows: (1) a cumulative $H_2$ production of 11.20 ml (in 110 ml of available headspace) in 183 hours; (2) a cumulative $H_2$ production rate of at least 0.556 ml/l-hour; and (3) a calculated $H_2$ concentration of 101.80 ml/l. This production assumes that the feedstock was not rate-limiting and the test started when the sterile medium was inoculated.

EXAMPLE 18

The thermophilic bacteria, *Thermosipho sp.* (DSMZ 6568) was placed in a sealed container along with DSMZ medium 613, a medium similar to the example medium above, and listed as one of the media that can be used for this invention. A pH of 7.0 was used glucose as the feedstock. The container had 50 ml of liquor with a headspace of 110 ml, consisting initially of nitrogen gas with 0.4–2% oxygen gas. The hydrogen gas production in the headspace may be described as follows: (1) a cumulative $H_2$ production of 13.1 ml (in 110 ml of available headspace) in 22 hours of incubation; (2) a cumulative $H_2$ production rate of 5.4 ml/l-hour; and a calculated $H_2$ concentration of 119 ml/l. This production assumes that the feedstock was not rate-limiting and that the tests started when the sterile medium was inoculated.

While the invention has been described with reference to details of the illustrated embodiment, these details are not intended to limit the scope of the invention as defined in the appended claims. For example, many species in the Order Thermotogales have been isolated from oil wells. Inasmuch as these organisms appear to be able to live and proliferate within the oil wells, then these organisms should be able to consume the organic matter found there, to produce the large amounts of $H_2S$ normally found at those depths. In fact, the inventors have found that these bacteria produce increased amounts of H2S when fed crude oil.

In light of the foregoing, a method for producing hydrogen is proposed wherein organisms from the Order Thermotogales are injected into tertiary oil wells that have been pre-treated in a manner that sequesters sulfides and elemental sulfur. Care is taken to maintain suitable pH, salinity, and temperature and perhaps pressure, of the spent well-turned reaction vessel. The envisioned process would facilitate consumption of residual oil which is no longer economically feasible for extraction. Harvesting procedures of the resulting hydrogen gas is effected via conventional means, i.e, vacuum, or sweeping with inert fluids.

In as much as the oil-feedstocks in these scenarios are several thousand feet below the earth's surface, any inhibiting effect due to the oxygen concentrations found at the earth's surface (i.e., 20 percent) is nonexistent.

What is claimed is:

1. A process for producing hydrogen comprising:
    a) providing a culture of a strain of a bacterium from the Order Thermotogales;
    b) culturing the strain in an enclosed vessel containing a feedstock, head source and an aqueous medium in a culturing environment, wherein the headspace of the vessel contains oxygen gas in a concentration of between 0.1 and 15 volumetric percent of the gas in the headspace of the vessel;
    c) maintaining the culturing environment at a temperature, pressure, and pH sufficient to allow the strain to metabolize the feedstock; and
    d) removing the hydrogen from the vessel during the culturing process.

2. The process as recited in claim 1 wherein the environment has no added sulfur or inorganic sulfide salts.

3. The process as recited in claim 1 wherein the environment is maintained at a temperature above 45° C.

4. The process as recited in claim 1 wherein the environment contains a feedstock selected from the group consisting of sugars, starches, xylans, celluloses, oils, petroleums, bitumens, amino acids, long-chain fatty acids, proteins, and combinations thereof.

5. The process of claim 1 wherein the aqueous medium has a dissolved oxygen gas concentration of between about 0.2 mg/liter and 2.8 mg/liter.

6. The process as recited in claim 1 wherein the environment is maintained at between 55° C. and 90° C.

7. The process as recited in claim 1 wherein the environment is maintained at a pH of between approximately 4 and 10.

8. The process as recited in claim 1 wherein the culture is a culture selected from the group consisting of *Thermotoga neapolitiana J., Petrotoga miotherma, Petrotoga mobilis, Thermotoga* sp. DSMZ 4138, *Thermotoga elfeii, Thermotoga hypogea, Thermosipho africanus, Fervidobacterium pennavorans, Thermotoga neapolitana, Thermotoga subterranea, Fervidobacterium gondwanense, Thermosipho melanesiensis, Thermotoga maritima, Thermotoga thermarum, Thermosipho* sp. DSMZ 6568, *Fervidobacterium islandicum, Fervidobacterium nodosum, Geotoga petraea, Geotoga subterranea*, and combinations thereof.

9. The process as recited in claim 1 wherein the process produces hydrogen gas and carbon dioxide in approximately a 2 to 1 ratio.

10. A method for producing hydrogen comprising:
    a) selecting a culture of a strain of a bacterium from the Order Thermotogales;
    b) culturing the strain in an environment in an enclosed vessel containing a feedstock, head space and an aqueous medium, wherein the medium contains oxygen gas in a concentration of between about 0.2 mg/liter and 2.8 mg/liter;
    c) maintaining the culturing environment at a temperature, pressure, and pH sufficient to allow the bacteria to metabolize the feedstock; and
    d) removing hydrogen from the vessel during the metabolism.

11. The process in claim 10 wherein the bacteria is a culture selected from the group consisting of *Thermotoga neapolitiana J., Petrotoga miotherma, Petrotoga mobilis, Thermotoga* sp. DSMZ 4138, *Thermotoga elfeii, Thermotoga hypogea, Thermosipho africanus, Fervidobacterium pennavorans, Thermotoga neapolitana, Thermotoga subterranea, Fervidobacterium gondwanense, Thermosipho melanesiensis, Thermotoga maritima, Thermotoga thermarum, Thermosipho* sp. DSMZ 6568, *Fervidobacterium islandicum, Fervidobacterium nodosum, Geotoga petraea, Geotoga subterranea*, and combinations thereof.

12. The method as recited in claim 10, wherein the feedstock is selected from the group consisting of sugars, starches, xylans, celluloses, and combinations thereof.

13. The method as recited in claim 10, wherein the feedstock is selected from the group consisting of oils, petroleums, bitumens, amino acids, long-chain fatty acids, proteins, and combinations thereof.

14. The method as recited in claim 10, wherein the environment is maintained at a temperature above 45° C.

15. The method as recited in claim 10, wherein the environment is maintained at a temperature of between 55° C. and 90° C.

16. The method as recited in claim 10, wherein the environment is maintained at a pH of between approximately 4 and 10.

17. The method as recited in claim 10, wherein the environment is preconditioned with an inert gas selected from a group consisting of helium, neon, argon, krypton, xenon, and combinations thereof.

18. The method as recited in claim 13 wherein the medium has no added sulfur or inorganic sulfide salts.

* * * * *